(12) United States Patent
Tisato et al.

(10) Patent No.: US 7,396,523 B2
(45) Date of Patent: Jul. 8, 2008

(54) RADIOACTIVE TRANSITION METAL-IMIDO HETERO-DIPHOSPHINE COMPLEXES, THEIR PREPARATION AND RADIOPHARMACEUTICAL COMPOSITIONS THEREOF

(75) Inventors: Francesco Tisato, Padua (IT); Cristina Bolzati, Jolanda di Savoja (IT); Marina Porchia, Padua (IT); Fiorenzo Refosco, Valdagno (IT)

(73) Assignee: Bracco Imaging S.p.A., Milan (IT)

( * ) Notice: Subject to any disclaimer, the term of this patent is extended or adjusted under 35 U.S.C. 154(b) by 0 days.

(21) Appl. No.: 10/533,988

(22) PCT Filed: Oct. 31, 2003

(86) PCT No.: PCT/EP03/12128

§ 371 (c)(1),
(2), (4) Date: Nov. 14, 2005

(87) PCT Pub. No.: WO2004/041311

PCT Pub. Date: May 21, 2004

(65) Prior Publication Data

US 2006/0120957 A1    Jun. 8, 2006

(30) Foreign Application Priority Data

Nov. 7, 2002    (EP) .................................. 02024803

(51) Int. Cl.
*A61K 51/00* (2006.01)
*A61M 36/14* (2006.01)
(52) U.S. Cl. .................... 424/1.65; 424/1.11; 424/1.37; 424/1.77
(58) Field of Classification Search ................ 424/1.65
See application file for complete search history.

(56) References Cited

U.S. PATENT DOCUMENTS 5,589,576 A * 12/1996 Archer et al. ................ 534/14

6,270,745 B1 * 8/2001 Duatti et al. ............... 424/1.77

FOREIGN PATENT DOCUMENTS

EP    0949265    10/1999
WO    WO 91/03262    3/1991

OTHER PUBLICATIONS

PCT International Search Report for PCT/EP03/12128 dated Apr. 15, 2004.
PCT International Preliminary Examination Report for PCT/EP03/12128 dated Jul. 6, 2004.
Arterburn et al. "Functionalized organomidorhenium(V) complexes as potential radiopharmaceuticals: syntheses of glycine derivatives and the structure determination of a rhenium analogue of chlorambucil" *Angewandte Chemie. International Edition*, vol. 35, No. 23/24, Jan. 3, 1997. (Abstract), incorrect year, no page numbers listed.
Arterburn et al. "Functionalized organomidorhenium(V) complexes as potential radiopharmaceuticals: syntheses of glycine derivatives and the structure determination of a rhenium analogue of chlorambucil" Angewandte Chemie. International Edition, vol. 35, No. 23/24, 1996, pp. 2877-2879.

* cited by examiner

*Primary Examiner*—Michael G. Hartley
*Assistant Examiner*—Melissa Perreira
(74) *Attorney, Agent, or Firm*—Kramer Levin Naftalis & Frankel LLP

(57) ABSTRACT

The present invention provides radioactive metal heterocomplexes of formula (I): $[(Me{=}N{-}R)L_1L_2]+Z$ (I), wherein Me, R, $L^1$ $L^2$ and $Z^-$ have the meanings indicated in the description. The complexes include a trivalent radioactive metal-imido group, typically a technetium- or rhenium-imido group, strongly stabilized by the presence of an ancillary tridentate hetero-diphosphine ligand $L^1$, which allows the formation of substitution-inert $[(Me{=}N{-}R)L^1]$ moieties. Such moieties are fixed in an intermediate $[(Me{=}N{-}R)Y_2L^1)]^+$ compound which contains two labile, cispositioned, Y ligands, where Y is preferably an halide group. The latter are easily replaced by a bidentate ligand $L^2$ to give the final $[(Me{=}N{-}R)L^1L^2]^+Z^-$ heterocomplexes. The complexes of the invention are useful for the preparation of radiopharmaceuticals: in fact, a bioactive fragment which confers biological target-seeking properties can be introduced either on the $L^2$ framework or the imido R group.

12 Claims, No Drawings

RADIOACTIVE TRANSITION METAL-IMIDO HETERO-DIPHOSPHINE COMPLEXES, THEIR PREPARATION AND RADIOPHARMACEUTICAL COMPOSITIONS THEREOF

This application is the national stage filing of corresponding international application number PCT/EP2003/012128, filed Oct. 31, 2003, which claims priority to and the benefit of European Application No. 02024803.5, filed Nov. 7, 2002, all of which are hereby incorporated by reference.

FIELD OF THE INVENTION

The present invention relates to a radioactive transition metal-imido heterocomplex, a radiopharmaceutical comprising said complex and a process for producing thereof. More particularly, the complex of the invention comprises an imido derivative of radioactive technetium or rhenium and two different ligands coordinated therewith.

STATE OF THE ART

The $^{99m}$Tc-imido core has been only generically cited among a series of new cores suitable for the development of technetium radiopharmaceuticals (Archer C. et al. WO 91/03262 and references therein). Despite a few examples obtained at "carrier added (ca)" or, in other words, macroscopic level, using $^{99}$Tc and cold Re, in which the presence of the imido group was clearly established, the transfer of this chemistry at "no carrier added (nca)" or, in other words, microscopic level, has met severe obstacles so far. The terms "macroscopic" or "carrier added" level refer to chemical reactions occurring at concentrations ranging from $10^{-3}$ to $10^{-5}$ M. Reactions are performed in conventional laboratories (if necessary approved for low level radioactivity) using from 1 to 200 mg amounts of non-radioactive Re or radioactive $^{99}$Tc. The terms "microscopic" or "no carrier added" level refer to reactions occurring at concentrations ranging from $10^{-6}$ to $10^{-9}$ M with micrograms to nanograms amounts of radioactive $^{99m}$Tc or of radioactive $^{188}$Re (see also IUPAC Compendium of Chemical Terminology, 2nd Edition (1997), wherein the following definition is provided for "no carrier added": " . . . a preparation of a radioactive isotope which is essentially free from stable isotopes of the element in question . . . "). These reactions are routinely performed in hospital Nuclear Medicine Departments for clinical purposes (Deutsch, E., Libson, K., *Recent advances in technetium chemistry: bridging inorganic chemistry and nuclear medicine*, Comments Inorg. Chem., 3, 83-103, 1984).

Working at macroscopic level with $^{99}$Tc, only five crystal structures of Tc(V)-imido species have been reported. They include [Tc(NR)Cl$_3$(PPh$_3$)$_2$], where R is phenyl (Nicholson T. et al. Inorg. Chim. Acta, 187 (1991) 51) or tolyl (Dilworth J. et al. in *Technetium in Chemistry and Nuclear Medicine*— 3, Raven Press, New York, (1990), 109). By varying the bulkiness of both the halide (from Cl to Br) and/or the phosphine (from PPh$_3$ to PMePh$_2$ and PMe$_2$Ph), three additional phenyl-imido compounds have been produced, i.e.: [Tc(NPh)Cl$_3$(PMePh$_2$)$_2$], [Tc(NPh)Br$_3$(PMePh$_2$)$_2$] (Rochon F. D. et al. Inorg. Chem. 34 (1995) 2273) and [Tc(NPh)Cl$_2$(PMe$_2$Ph)$_3$]$^+$ (Nicholson T. et al. Inorg. Chim. Acta, 230 (1995) 205).

Nevertheless, no specific disclosure, nor even suggestions, have ever been made on the possibility of successfully transferring the above preparations also at microscopic level.

All the above species are six-coordinated compounds with slight distortion from the ideal octahedron. The co-ordination sphere is totally filled with monodentate ligands (halides and monophosphines) that do not impose heavy steric constraints. In this connection the Tc atom moves off the mean basal plane towards the imido unit by only 0.11 Å. The imido core is essentially linear (mean Tc=N—C angle 175.7°) with a marked portion of the Tc—N bond showing double bond character (mean value 1.71 Å; see G. Bandoli et al., *Coord. Chem. Rev.*, 214 (2001) 43).

The possibility to introduce chelate ligands in the co-ordination sphere of Tc(V)-imido compounds was demonstrated separately by different authors. Nicholson et al. (*Inorg. Chim. Acta*, 196 (1992) 27) introduced a simple bidentate diphosphine, i.e. 1,2-bis (diphenylphosphine)ethane (dppe) to yield [Tc(NPh)Cl$_3$(dppe)]. Tisato et al. (*J. Organom. Chem.* 637-639 (2001) 772) utilised the 1,2-bis (diphenylphosphine)ferrocenyl residue (dppf) to produce the analogous [Tc(NPh)Cl$_3$(dppf)] complex. Similarly, rhenium (Re) complexes where synthesized, by using the bidentate (2-diphenylphosphine) benzeneamine (H$_2$dpa), or the tetradentate N,N'-bis[(2-diphenylphosphine)phenyl]propane-1,3-diamine (Refosco F. et al, *J. Chem. Soc. Dalton Trans* 1998, 923-930).

Notwithstanding the above results, successive extensive efforts to stabilize the $^{99m}$Tc-imido core have surprisingly failed, because no appropriate combinations of donor atoms was found to support this group, while, on the contrary, this target was successfully achieved in the case of the somewhat similar $^{99m}$Tc-oxo and $^{99m}$Tc-nitrido cores. Oxo [$^{99m}$Tc(O)]$^{3+}$, imido [$^{99m}$Tc(NR)]$^{3+}$ and nitrido [$^{99m}$Tc(N)]$^{2+}$ moieties are isoelectronic cores, the metal being in the 5$^+$ oxidation state, and, in this connection, the technetium-imido group can be considered as intermediate between oxo and nitrido cores. Previous investigations have established that Tc(V)-oxo groups are readily stabilized by tetradentate ligands, as shown by N$_4$-hexamethylpropylene amine oxime (HM-PAO), N$_3$S-mercaptoacetyltriglycyl (MAG$_3$) and N$_2$S$_2$-ethylcysteine dimer (ECD) in the clinically used Ceretec®, Technescan® and Neurolite® radiopharmaceuticals. On the other hand, the Tc(V)-nitrido group prefers a combination of two different polydentate ligands. Previous studies on $^{99}$Tc-imido complexes have shown that distorted octahedral environments are usually achieved, the coordination being supported by monodentate ligands, preferably tertiary monophosphines and halides. Attempts to replace the monodentate P-based donors present in the prototype precursor [Tc(NPh)Cl$_3$(PPh$_3$)$_2$] with various polydentate chelates were not successful, thus indicating that the imido group should be stabilized only by the presence of monodentate monophosphine ligands.

DESCRIPTION OF THE INVENTION

It has now surprisingly been found that it is possible to replace the two monodentate triphenylphosphine substituents with a tridentate heterodiphosphine ligand L$^1$ which comprises an electron donor heteroatom in the spacer chain linking said two phosphine groups, without affecting the stability of the imido group in the resulting [(Me=N—R)Y$_2$(L$^1$)]$^+$Y$^-$ compounds, wherein Y is a leaving group, such as a halogen atom, an hydroxy or an alkoxy group. The facial configuration of the tridentate hetero-diphosphine chelate induces a cis-coordination of the two Y groups, which in turn can be easily substituted with suitable bidentate ligands L$^2$ to give the final desired [(Me=N—R)L$^1$L$^2$]$^+$Z$^-$ metal heterocomplex.

Accordingly, the present invention primarily provides a radioactive transition metal-imido hetero-diphosphine complex compound of formula (I):

$$[(Me=N-R)L^1L^2]^+Z^- \qquad (I),$$

wherein:

Me is a radioactive transition metal selected from the group consisting of $^{99m}Tc$, $^{186}Re$, $^{188}Re$;

R is a $C_1$-$C_{15}$ linear or branched alkyl or alkenyl residue, optionally interrupted by —O—, —S—, —N(R')—, where R' is H or $C_1$-$C_6$ alkyl, and/or optionally substituted with halogen, hydroxy, $C_1$-$C_5$ alkoxy, carboxy, ester, thiol, primary or secondary amino or amido groups, or R is phenyl or an aryl residue, being R optionally substituted with a biologically active substance, wherein said biologically active substance is selected among sugars, amino acids, fatty acids, vitamins, hormones, peptides, catecholamines, said catecholamines being optionally conjugated, via peptidic bond, to the other above mentioned biologically active substances;

$L^1$ is a tridentate hetero-diphosphine ligand of formula (II):

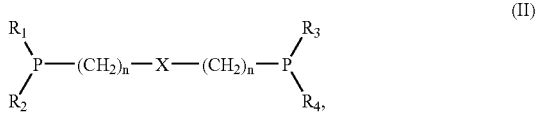

wherein:

$R^1$, $R^2$, $R^3$ and $R^4$, which may be the same or different, have the same meanings as R;

X is oxygen, sulphur, $NR^5$, wherein $R^5$ is hydrogen or R;

n is an integer ranging from 1 to 5;

$L^2$ is a bidentate ligand, which comprises a combination of two donor atoms, selected from the group consisting of oxygen, sulphur and nitrogen, said atoms being preferably negatively charged and being separated by a spacer of 2 to 4 members, said spacer being an aliphatic chain or part of an aromatic ring, $L^2$ being optionally conjugated to a biologically active substance as above defined;

$Z^-$ is a mononegative counter-ion selected from the group consisting of $Cl^-$, $Br^-$, $OH^-$, $ClO_4^-$, alkoxylate, preferably $EtO^-$, tetrafluoroborate.

Preferred R are methyl, ethyl, propyl, isopropyl, butyl, isobutyl, octyl, decyl, dodecyl, propenyl, butenyl, pentenyl, phenyl, benzyl, tolyl, 4-methoxy-benzyl, 4-ethoxy-benzyl, salicyl.

Preferred tridentate hetero-diphosphine ligands $L^1$ of formula (II) are those where n=2. Most preferred ligands $L^1$ are selected from the group consisting of:

$(C_6H_5)_2PCH_2CH_2N(H)CH_2CH_2P(C_6H_5)_2$;
$(C_6H_5)_2PCH_2CH_2N(CH_3)CH_2CH_2P(C_6H_5)_2$;
$(CH_3)_2PCH_2CH_2N(CH_3)CH_2CH_2P(CH_3)_2$;
$(C_6H_5)_2PCH_2CH_2SCH_2CH_2P(C_6H_5)_2$;
$(C_6H_5)_2PCH_2CH_2OCH_2CH_2P(C_6H_5)_2$;
$(C_6H_5)_2PCH_2CH_2N(CH_2CH_2OCH_3)CH_2CH_2P(C_6H_5)_2$.

Bidentate ligands $L^2$ preferably comprise a 2 or 3 membered spacer as defined above between the two electron-donor atoms. Suitable combinations of electron-donor atoms, preferably negatively charged, are $[O^-,O^-]$, $[N^-,O^-]$, $[S^-,O^-]$, $[N^-,N^-]$, $[N^-,S^-]$ and $[S^-,S^-]$. Preferred bidentate ligands are catecholate$^{(2-)}$; carbonate$^{(2-)}$; 1,2-aminophenolate$^{(2-)}$; 1,2-benzenedithiolate$^{(2-)}$; ethyleneglycolate$^{(2-)}$; ethylenediaminate$^{(2-)}$; ethylenedithiolate$^{(2-)}$; 1,2-phenylenediaminate$^{(2-)}$; 1,2-aminothiophenolate$^{(2-)}$; thiosalicylate$^{(2-)}$; 1,2-aminoethanolate$^{(2-)}$ and the like.

The bidentate ligands $L^2$ preferably carry a biologically active substance as defined above. Among said biologically active substances, preferred are catecholamines, like dopamine, L-DOPA and 3-hydroxytyramine. Catecholamines may, in turn, be conjugated, via peptidic bond, to other physiologically active substances. In a preferred embodiment of the invention, vitamin H is conjugated to dopamine.

The radioactive compounds of formula (I) can be obtained by reacting an intermediate compound of formula (III):

$$[(Me\!=\!\!N\!-\!R)Y^2(L^1)]^+Y^- \quad (III),$$

with a bidentate ligand $L^2$, wherein Me, R, $L^1$ and $L^2$ are as defined above and Y is halogen, preferably chlorine, or bromine, hydroxy or alkoxy, preferably ethoxy, or a leaving group which easily undergoes nucleophilic substitution.

The reaction is usually carried out in an organic solvent, in the presence of an organic base, or under buffered conditions, preferably in phosphate buffer. Preferred solvents are alcohols and chlorinated solvents. Preferred organic bases are tertiary amines, more preferred is triethylamine. The reaction temperature ranges from room temperature to the reflux temperature of the solvent.

The final product is separated and purified with conventional techniques like salification, crystallization, chromatography as described in detail in the following experimental section.

Intermediate compounds of formula (III) are in turn synthesized as described in Scheme 1 below from oxides of radioactive transition metals, preferably $^{99m}TcO_4^-$, $^{186}ReO_4^-$, or $^{188}ReO_4^-$, more preferably $^{99m}TcO_4^-$, which are treated with an excess of tertiary monophosphines, preferably $PPh_3$, in acidic hydro-alcoholic solutions and in the presence of a suitable imido donor (D), to give an imido complex of formula (IV), wherein Me, R and Y are as defined above. Successive treatment with an above described ligand $L^1$ affords the desired intermediates of formula (III).

Scheme 1

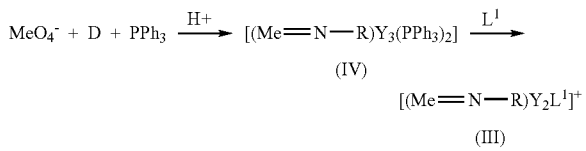

Suitable imido donors D according to the invention are preferably 1-substituted-2-acetyl hydrazine, most preferably 1-phenyl-2-acetyl hydrazine (PAH).

The reaction of $L^1$ with imido complexes of formula (IV) is preferably carried out in organic solvents like alcohols, chlorinated solvents, acetonitrile or a mixture thereof, optionally in the presence of an organic base like triethylamine, at a temperature ranging from room temperature to the reflux temperature of the solvent. The final purification of the desired intermediate of formula (III) is thoroughly described in the following experimental section. It has finally been demonstrated that the preferred $^{99m}Tc$-imido heterocomplexes according to the invention can be obtained at microscopical level via a three-step approach starting from pertechnetate sodium salt eluted from a commercial $^{99}Mo/^{99m}Tc$ generator. In the first step pertechnetate is treated with an excess of tertiary monophosphine in hydro-alcoholic solutions acidified with hydrochloric acid and in the presence of 1-phenyl-2-acetyl hydrazine. In the second step, addition of the tridentate hetero-diphosphine ligand in an organic solvent affords the intermediate species $[^{99m}Tc(NPh)Cl_2(L^1)]^+Y^-$. By adjusting pH at 7.4 with phosphate buffer, and by adding the preferred bidentate ligand $L^2$, the desired imido heterocomplex is produced in high radiochemical yield (see Table 1).

Preferred complexes of the invention are:
[$^{99m}$Tc(NPh)(PNHP)(O,N-ap)];
[$^{99m}$Tc(NPh)(PNHP)(O,O-car)];
[$^{99m}$Tc(NPh)(PNMeP)(O,N-ap)];
[$^{99m}$Tc(NPh)(PNMeP)(S,N-atp)];
[$^{99m}$Tc(NPh)(PNMeP)(O,O-cat)];
[$^{99m}$Tc(NPh)(PNMeP)(S,O-tsal)];
[$^{99m}$Tc(NPh)(PNMeP)(S,S-bdt)];

wherein
PNHP means $(C_6H_5)_2PCH_2CH_2N(H)CH_2CH_2P(C_6H_5)_2$;
PNMeP means $(C_6H_5)_2PCH_2CH_2N(CH_3)CH_2CH_2P(C_6H_5)_2$;
O,N-ap means 2-aminophenolate$^{(2-)}$;
S,N-atp means 2-aminothiophenolate$^{(2-)}$;
O,O-cat means catecholate$^{(2-)}$;
O,O-car means carbonate$^{(2-)}$;
S,O-tsal means thiosalicylate$^{(2-)}$;
S,S-bdt means 1,2-benzenedithiolate$^{(2-)}$ The reactivity of imido-containing species has been thoroughly studied at macroscopic level using [$^{99}$Tc(NPh)Cl$_3$(PPh$_3$)$_2$] and [Re(NPh)Cl$_3$(PPh$_3$)$_2$] as precursors.

These precursors react with tridentate hetero-diphosphine ligands $L^1$ to yield intermediate compounds of the type [Me(NPh)Cl$_2$L$^1$)][Cl]. The hetero-diphosphine ligand acts as a tridentate donor due to the presence of the electron-donor X heteroatom interposed in the diphosphine chain and gives rise to three different octahedral configurations, shown by the following formulas (IIIA): fac,cis (IIIB) mer,cis and (IIIC) mer,trans.

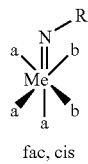

fac, cis (IIIA)

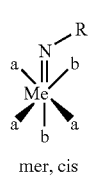

mer, cis (IIIB)

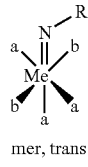

mer, trans (IIIC)

In formulae (IIIA), (IIIB) and (IIIC) a denotes the positions occupied by ligand $L^1$ and b denotes the positions occupied by ligand Y.

The halide group, positioned trans with respect to the imido core in the intermediate mer,cis-[Me(NPh)Cl$_2$(L$^1$)]$^+$ compounds, easily undergoes substitution with nucleophilic ligands (such as ethanolate), indicating that halide ligands are labile and good leaving groups. In similar substitution reactions, cis-positioned halides are replaced by bidentate nucleophilic ligands such as ethyleneglycol or catechol or the like to yield imido heterocomplexes of the type [Me(NPh)L$^1$L$^2$]$^+$Z$^-$. Thus, both mer,cis-[Me(NPh)Cl$_2$L$^1$]$^+$ and fac,cis-[Me(NPh)Cl$_2$L$^1$]$^+$ isomers are useful intermediates for the production of mixed imido heterocomplexes. On the contrary, the mer, trans-[Me(NPh)Cl$_2$L$^1$]$^+$ isomers give rise to the heterocomplexes in a negligible yield, as a result of heavy steric constraints imposed by the meridional coordination of the $L^1$ diphosphine combined with the trans-halide configuration. Thus, a reciprocal cis-position of the halide groups in the intermediate compounds is an essential pre-requisite for obtaining heterocomplexes of the invention.

The stereochemistry of the $L^1$ ligand in the final heterocomplex is always facial, the bidentate ligand $L^2$ filling the residual two positions on the equatorial plane of the octahedron.

The present invention is illustrated in further detail in the following examples.

EXAMPLES

The tridentate hetero-diphosphine ligands $L^1$ and the bidentate ligands $L^2$ used in the following examples are abbreviated as follows:

Tridentate hetero-diphosphine ligands $L^1$:
PNHP; $(C_6H_5)_2PCH_2CH_2N(H)CH_2CH_2P(C_6H_5)_2$
PNMeP; $(C_6H_5)_2PCH_2CH_2N(CH_3)CH_2CH_2P(C_6H_5)_2$
MePNMePMe; $(CH_3)_2PCH_2CH_2N(CH_3)CH_2CH_2P(CH_3)_2$
PNOMeP; $(C_6H_5)_2PCH_2CH_2N(CH_2CH_2OCH_3)CH_2CH_2P(C_6H_5)_2$
POP; $(C_6H_5)_2PCH_2CH_2OCH_2CH_2P(C_6H_5)_2$
PSP; $(C_6H_5)_2PCH_2CH_2OCH_2CH_2P(C_6H_5)_2$ Bidentate ligands $L^2$:
O,O-cat; catecholate$^{(2-)}$
O,O-car; carbonate$^{(2-)}$
N,N-pda; 1,2-phenylenediaminate$^{(2-)}$
S,S-bdt; 1,2-benzenedithiolate$^{(2-)}$
O,O-eg; ethyleneglycolate$^{(2-)}$
N,N-en; ethylenediaminate$^{(2-)}$
S,S-edt; ethylenedithiolate$^{(2-)}$
O,N-ap; 1,2-aminophenolate$^{(2-)}$
S,N-atp; 1,2-aminothiophenolate$^{(2-)}$
O,S-tsal; thiosalicylate$^{(2-)}$
O,N-ae; 1,2-aminoethanolate$^{(2-)}$ Chemistry at macroscopic (ca) level by using $^{99}$Tc and Re Example 1

Synthesis of mer,cis-[$^{99}$Tc(NPh)Cl$_2$(PNEP)][Cl]

To a solution of [Tc(NPh)Cl$_3$(PPh$_3$)$_2$] (45 mg) in dichloromethane/methanol (5 mL/1 mL) a 1.1 equivalent of solid PN(H)P was added under stirring. The brown mixture, in 2 minutes, turned brown-green. After 3 h the solution was taken to dryness with a flow of nitrogen. The oily residue was treated with diethyl ether and the resulting brown-green solid filtered. The crude solid was washed on the filter with acetone (2 mL). The light green solid was dried under nitrogen (yield 22 mg, 60%). The product is soluble in chlorinated solvents and acetonitrile, slightly soluble in alcohols, insoluble in diethyl ether.

$^{31}$P-NMR (300 MHz, CDCl$_3$, ppm): 31.6 (bs).
$^1$H-NMR (300 MHz, CDCl$_3$, ppm): 9.70 (bs, 1H; N—H), 8.06 (m, 4H, PPh$_2$), 7.51 (m, 13H, PPh$_2$+NPhγ,α), 7.02 (m, 6H, PPh$_2$), 6.86 (t, 2H, NPhp), 3.97 (bt, 2H, CH$_2$), 3.34 (bm, 6H, CH$_2$).

Example 2

Synthesis of mer,cis-[Re(NPh)Cl$_2$(PNHP)][Cl]

To a suspension of [Re(NPh)Cl$_3$(PPh$_3$)$_2$] (104 mg, 0.11 mmol) in CH$_2$Cl$_2$, an excess of PNHP.HCl (75 mg, 0.16 mmol) dissolved in CH$_2$Cl$_2$ with 50 µl of NEt$_3$ (0.38 mmol) was added dropwise. The reaction mixture was refluxed for 2 hours and then stirred overnight at room temperature. The resulting solution was olive-green. The solvent was removed and the green solid washed with diethyl ether, water and dried under vacuum. The $^{31}$P-NMR spectrum of such solid in CDCl$_3$ showed two peaks at 4.3 an 8.4 ppm, which suggest the presence of two new products. A pure product was obtained by crystallization from a CH$_2$Cl$_2$/n-hexane mixture. Grey-blue crystals were obtained (final yield 30-40%) and the compound was identified as [Re(NPh)Cl$_2$(PN(H)P)]Cl. The product is stable in air and soluble in CH$_2$Cl$_2$, CHCl$_3$, quite soluble in EtOH and MeOH, insoluble in H$_2$O, hexane and Et$_2$O.

$^{31}$P-NMR (300 MHz, CDCl$_3$, ppm): 8.48 (s).

$^1$H-NMR (300 MHz, CDCl$_3$, ppm): 8.07(m, 4H, PPh$_2$), 7.71 (d, 2H,), 7.50 (m, 11H, PPh$_2$+NPhγ), 7.03 (m, 6H, PPh$_2$), 6.87 (t, 2H, NPhβ), 4.01 (bt, 2H, CH$_2$), 3.39 (bm, 2H, CH$_2$), 3.22 (bm, 4H, CH$_2$), 9.5 (b, 1H, NH).

Example 3

Synthesis of mer,cis-[Re(NPh)(OEt)Cl(PNHP)][Cl]

To a suspension of [Re(NPh)Cl$_3$(PPh$_3$)$_2$] (52 mg, 0.057 mmol) in EtOH, an excess of PNHP.HCl (43 mg, 0.089 mmol) dissolved in EtOH with 25 µl of NEt$_3$ (0.19 mmol) was added dropwise. The reaction mixture was refluxed for 4 hours: the resulting solution was green-yellowish. The volume was reduced under a nitrogen stream and Et$_2$O was added: after few hours large bright blue crystals of [Re(NPh)(OEt)Cl(PNHP)]Cl had been formed.

$^{31}$P-NMR (300 MHz, CDCl$_3$, ppm): −0.20 (s).

$^1$H-NMR (300 MHz, CDCl$_3$, ppm): 9.5 (b, 1H, NH), 8.00 (m, 4H, PPh$_2$), 7.53 (m, 13H, PPh$_2$+NPh), 7.07 (m, 6H, PPh$_2$), 6.87 (t, 2H, NPhpβ), 3.99 (bt, 2H, CH$_2$), 3.41 (m, 2H, CH$_2$), 3.18 (m, 2H, CH$_2$), 2.98 (m, 2H, CH$_2$), 2.64 (q, 2H; O—CH$_2$—CH$_3$), -0.13 (t, 3H; O—CH$_2$—CH$_3$).

Example 4

Synthesis of fac,cis-[Re(NPh)Cl$_2$(PNMeP)][Cl]

To a suspension of [Re(NPh)Cl$_3$(PPh$_3$)$_2$] in CH$_2$Cl$_2$ a slight excess of PNMeP (86 mg, 0.19 mmol) was added. The reaction mixture was refluxed for 24 h. The volume of the resulting green-yellowish solution was reduced and Et$_2$O was added. A TLC analysis of the precipitate showed a mixture of different products, so separation by means of a cromatographic column was performed (silica gel, CHCl$_3$/EtOH 3/2). Two yellow and a green fraction were collected. The green product was identified as [Re(NPh)Cl$_2$(PNMeP)]Cl.

$^{31}$P{H}-NMR (300 MHz, CDCl$_3$, ppm): 19.9 (s).

$^1$H-NMR (300 MHz, CDCl$_3$, ppm): 4.08, 3.45 and 2.95 (m, 8H CH$_2$), 2.61 (s, 3H, CH$_3$).

Example 5

Synthesis of mer,trans-[Re(NPh)Cl$_2$(PNMeP)][Cl]

[Re(NPh)Cl$_3$(PPh$_3$)$_2$] (100 mg, 0.11 mmol) and PNMeP.HCl (86 mg, 0.17 mmol) were mixed in acetonitrile. By refluxing for 15 minutes the reaction mixture became light green. Additional reflux deposited a green solid within a few hours. After 4 h the mixture was allowed to reach room temperature and filtered. The green powder was washed with Et$_2$O and resulted soluble in CH$_2$Cl$_2$, quite soluble in CHCl$_3$ and almost insoluble in Et$_2$O and benzene. NMR analysis evidenced the presence of two isomers in solution (yield 70%), then characterised as cis-[Re(NPh)Cl$_2$(PNMeP)]Cl.HCl. $^1$H-NMR (300 MHz, CD$_2$Cl$_2$, ppm): 6.59 (d); 6.74 (t); 7.45 (t) (5H, NPh); 7.10 (m); 7.24 (m); 7.37 (m); 7.55 (m); 7.70 (m); 7.85 (m); 7.96 (m) (20H, PPh$_2$); 3.74(m); 3.35 (m); 3.08 (m) (8H, CH$_2$); 2.99 (d); 2.69 (d) CH$_3$.$^{31}$P {H} NMR (300 MHz,CD$_2$Cl$_2$,ppm): −25.1 (s); −26.9 (s). The pale-green powder (cis-[Re(NPh)Cl$_2$(PNMeP)]Cl.HCl) was dissolved in CH$_2$Cl$_2$ in the presence of an excess of NEt$_3$. NMR analysis evidenced the quantitative conversion into the mer,trans-[Re(NPh)Cl$_2$(PNMeP)]Cl complex.

$^{31}$P-NMR (300 MHz, CDCl$_3$,ppm): 19.9 (s)

$^1$H-NMR (CDCl$_3$, ppm)=7.6-7.1 (20H; PPh$_2$) 4.08, 3.45 and 2.95 (m, 8H; methylene protons); 2.61 (s, 3H; CH$_3$).

Example 6

Synthesis of fac-[$^{99}$Tc(NPh)(O,O-cat)(PNHP)][ClO$_4$]

To a solution of [$^{99}$Tc(NPh)Cl$_2$(PNHP)][Cl], prepared according to Example 1, (26 mg, 0.04 mmol) in methanol (5 mL), catechol (5.2 mg, 0.047 mmol) and triethylamine (6.7 µL, 0.047 mmol) were added. The colour of the mixture turned immediately deep purple. The solution was stirred for 4 h and concentrated to 2 mL by a nitrogen flow. A drop of a saturated NaClO$_4$ solution in MeOH was added to the solution. After 1 day, dark-grey crystals were formed; they were collected on a filter and washed with a 1×2 mL of MeOH.

$^{31}$P-NMR (300 MHz, CDCl$_3$, ppm): 46.5 (bs).

$^1$H-NMR (300 MHz, CDCl$_3$, ppm): 7.77 (t, 4H), 7.49 (t, 4H,), 7.40 (t, 4H), 7.22 (m, 6H) 7.02 (m, 7H), 6.87 (m, 2H), 6,71 (m, 2H), 3.5-2.7 (8H).

Example 7

Synthesis of fac-[Re(NPh)(O,O-cat)(PNHP)][Cl]

To a bluish solution of [Re(NPh)Cl$_2$(PNHP)]Cl, prepared according to Example 2, in CH$_2$Cl$_2$ (40 mg, 0.05 mmol) catechol (H$_2$cat) (5 mg, 0.045 mmol) and 20 µl of NEt$_3$ were added at room temperature. The reaction mixture immediately turned red. The solution was stirred overnight at room temperature. After 15 h the solvent was removed, the residue was treated with diethyl ether and the resulting red-brown solid filtered and washed several times with n-hexane, diethyl ether and water. [Re(NPh)(O,O-cat)(PNHP)]Cl was obtained with a final yield of 53%. $^1$H-NMR (300 MHz, CDCl$_3$): 7.85-7.07 (m, 25H, NPh and PPh$_2$), 6.91-6.73 (m, 4H, catH).

$^{31}$P-NMR: 19.5 (s). A stoichiometric amount of NBu$_4$BF$_4$ was added to a CH$_2$Cl$_2$ solution of [Re(NPh)(O,O-cat)(PNHP)]Cl and by addition of n-hexane a red-orange product precipitated. Accoprding to the elemental analysis, this powder was characterized as the tetrafluoroborate salt of [Re(NPh)(O,O-cat)(PNHP)]

$^{31}$P-NMR: 19.5 (s).

El. Anal.: ReN$_2$C$_{40}$H$_{38}$O$_2$P$_2$BF$_4$, MW 913.7

Calcd. C 52.6, N 3.2, H 5.1

Found: C 52.9, N 3.2, H 5.1.

Example 8

Synthesis of fac-[Re(NPh)(O,O-eg)(PNHP)][Cl]

To a bluish solution of [Re(NPh)Cl$_2$(PNHP)]Cl of Example 2 in CH$_2$Cl$_2$ (40 mg, 0.05 mmol) 30 µl of ethylene glycol and 20 µl of NEt$_3$ were added at room temperature. The reaction mixture was refluxed for 1 h and then stirred at room temperature for 24 h. The solution became grey. After removal of the solvent with a gentle nitrogen stream, the oily residue was treated with diethyl ether and the resulting grey solid filtered. The crude solid was purified washing, on the filter, with n-hexane and water. Grey crystals of [Re(NPh)(O,O-eg)(PNHP)]Cl, suitable also for X-ray diffractometric analysis, were obtained by crystallization from a CH$_2$Cl$_2$/n-hexane solution. $^{31}$P {H} NMR (300 MHz, CD$_2$Cl$_2$) 17.2. $^1$H-NMR (300 MHz, CDCl$_3$): 7.74-6.91 (m, 25H, NPh and PPh$_2$), 4.98 (b, 1H, NH), 4.78 (d, 2H, CH$_2$), 4.60 (d, 2H, CH$_2$), 3.2-2.9 (m, 8H, PCH$_2$CH$_2$N).

Example 9

Synthesis of fac-[Re(NPh)(O,O-eg)(PNMeP)][Cl]

To a solution of fac,cis-[Re(NPh)Cl$_2$(PNMeP)]Cl of Example 4 in CH$_3$CN (50 mg, 0.06 mmol) 30 µl of ethylene glycol and 20 µl of NEt$_3$ were added. The reaction mixture was refluxed for 24 h. The volume of the dark green solution was reduced and the oily residue was dissolved in CH$_2$Cl$_2$, The excess of ethylene glycol was removed by water extraction. The organic phase was dried and a green powder, characterised as fac-[Re(NPh)(O,O-eg)(PNMeP)]Cl was recovered (yield 43%).

$^1$H-NMR (300 MHz, CDCl$_3$, δ ppm): 6.98-7.48 (m, 25H, NPh and PPh$_2$); 4.91-4.76 (m, 4H CH); 3.58 (m), 3.27 (m) e 2.27 (m) (8H, —CH$_2$CH$_2$—PNP; 2.34 (s,3H,N—CH$_3$).

$^{31}$P(CDCl$_3$):=24.3 (s).

Example 10

Synthesis of fac-[Re(NPh)(O,N-ap)(PNMeP)][Cl]

To a suspension of [Re(NPh)Cl$_3$(PPh$_3$)$_2$] in CH$_2$Cl$_2$ (90 mg, 0.1 mmol) PNMeP (53 mg, 0.11 mmol) was added at room temperature. After 5 minutes 1,2 aminophenol (17 mg, 0.16 mmol) and 20 µl of NEt$_3$ were added and the reaction mixture was refluxed. After 10 minutes the solution turned from green to dark brown. After refluxing for 30 min the solution was stirred overnight at room temperature. The solvent was removed and the residue treated with diethyl ether. The red brown solid was filtered and re-dissolved in CH$_2$Cl$_2$. Elution from a silica column with CHCl$_3$/MeOH 85/15 separated a yellow by-product and the red fac-[Re(NPh)(O,N-ap)(PNMeP)]Cl.

$^{31}$P(CDCl$_3$):=17.8 (d), 10.1 (d).

Chemistry at microscopic (nca) level by employing $^{99m}$Tc)

Example 11

Synthesis of the Intermediate [$^{99m}$Tc(NPh)Cl$_2$ L$^1$)]$^+$ Y$^-$.

0.1 mL of saline physiological solution containing [$^{99m}$TcO$_4$]$^-$ (50 Mbq) were added to a vial containing 10 mg of PAH, 3 mg of PPh$_3$ 0.1 mL of 1 M HCl and 1.5 mL of MeOH. The resulting solution was heated at 65° C. for 30 min. After this, 0.2 mL of an alcoholic solution containing 3 mg of an appropriate L$^1$ hetero-diphosphine ligand (PNHP or PNMeP or PNOMeP) was added. The resulting solution was maintained at 65° C. for further 30 min.

TLC analysis of the intermediate [$^{99m}$Tc(NPh)Cl$_2$L$^1$)]$^+$ species showed a mixture of different products. This behaviour is in agreement with the evidences produced at macroscopic level, where some intermediate species were characterised.

Example 12

Synthesis of [$^{99m}$Tc(NPh)L$^1$L$^2$]$^+$Z$^-$.

This three-step preparation involves the preliminary formation of a mixture of intermediate complexes of general formula [$^{99m}$Tc(NPh)Y$_2$L$^1$] (Y=halides, water, hydroxyl, alkoxy) followed by its conversion into the final asymmetrical compound by reactions with the bidentate ligand L$^2$. In detail, 0.250 mL of phosphate buffer 1 M, pH 7.4, followed by 0.2 mL of methanol solution containing 5 mg of an appropriate bidentate ligand L$^2$ were added to the vial containing the intermediate compound, obtained as reported above. The mixture was heated at 65° C. for 1 h. The radiochemical yields evaluated by TLC chromatography are reported in Table 1.

TABLE 1

| Complexes | TLC, Rf | Yield % |
|---|---|---|
| [$^{99m}$Tc(NPh)(PNHP)(O,N-ap)] | 0.42$^b$ | 62 |
| [$^{99m}$Tc(NPh)(PNMeP)(O,N-ap)] | 0.24$^a$; 0.45$^b$; 0.14$^c$ | 97 |
| [$^{99m}$Tc(NPh)(PNMeP)(S,N-atp)] | 0.28$^a$; 0.28$^c$ | 85 |
| [$^{99m}$Tc(NPh)(PNMeP)(O,O-cat)] | 0.85$^a$; 0.85$^c$; 0.5$^d$ | 91 |
| [$^{99m}$Tc(NPh)(PNMeP)(S,O-tsal)] | 0.78$^a$; 0.75$^c$, 0.35$^d$ | 90 |
| [$^{99m}$Tc(NPh)(PNMeP)(S,S-bdt)] | 0.74$^a$; 1$^{b,c,d}$ | 98 |

TLC SiO$_2$:
$^a$EtOH/CHCl$_3$/C$_6$H$_6$ (1/2/1.5);
$^b$CHCl$_3$/MeOH (2% NH$_4$OH 20%) 85/15;
$^c$CHCl$_3$/MeOH (2% NH$_4$OH 20%) 90/10;
$^d$CHCl$_3$/MeOH (2% NH$_4$OH 20%) 95/5

Rf values shown by the compounds of Table 1 are in full accord with the ones shown by the corresponding compounds obtained at macroscopic level, using $^{99}$Tc, thus confirming that for the compounds of the invention the transfer from macro to micro level is possible.

The metal-imido hetero-diphosphine complexes of the present invention proved useful in the radiopharmaceutical field, either in radiodiagnostic imaging, when $^{99m}$Tc is the employed radioactive metal, or in radiotherapy, when $^{186}$Re and $^{188}$Re are the radioactive metals.

Accordingly, the invention encompasses also the use of these complexes in the diagnostic and/or therapeutic radiopharmaceutical field and the pharmaceutical compositions comprising said compounds in admixture with pharmaceutically acceptable carriers and/or excipients.

The invention claimed is:

1. A radioactive transition metal-imido hetero-diphosphine complex compound of formula (I):

[(Me≡N—R)L¹L²]⁺Z⁻  (I), wherein:
Me is a radioactive transition metal selected from the group consisting of $^{99m}$Tc, $^{186}$Re, $^{188}$Re;
R is selected from the group consisting of methyl, ethyl, propyl, isopropyl, butyl, isobutyl, octyl, decyl, dodecyl, propenyl, butenyl, pentenyl, phenyl, benzyl, tolyl, 4-methoxy-benzyl, 4-ethoxy-benzyl, and salicyl, wherein R is substituted with a biologically active substance, said substance being a catecholamine selected from the group consisting of dopamine, L-DOPA, 3-hydroxytyramine, optionally conjugated, via peptide bond, to another biologically active substance selected from the group consisting of sugars, amino acids, fatty acids, vitamins, hormones, peptides, and catecholamines;
L¹ is a tridentate hetero-diphosphine ligand of formula (II):

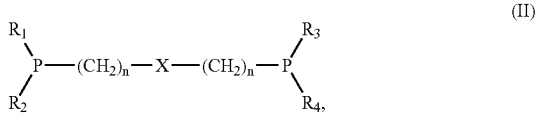

wherein:
R¹, R², R³ and R⁴, which may be the same or different, are:
  a $C_1$-$C_{15}$ linear or branched alkyl or alkenyl residue optionally interrupted by —O—, —S—, —N(R')—, where R'=H or $C_1$-$C_6$ alkyl, and/or optionally substituted with halogen, hydroxy, $C_1$-$C_5$ alkoxy, carboxy, ester, thiol, primary or secondary amino or amido, groups, or
  a phenyl or an aryl residue, R¹, R², R³ and R⁴ being optionally substituted with a biologically active substance, wherein said biologically active substance is selected among sugars, amino acids, fatty acids, vitamins, hormones, peptides and catecholamines, said catecholamines being optionally conjugated, via peptidic bond, to another of the above mentioned biologically active substances;
X is oxygen, sulphur, NR⁵, wherein
R⁵ is:
  hydrogen,
  a $C_1$-$C_{15}$ linear or branched alkyl or alkenyl residue optionally interrupted by —O—, —S—, —N(R')—, where R'=H or $C_1$-$C_6$ alkyl, and/or optionally substituted with halogen, hydroxy, $C_1$-$C_5$ alkoxy, carboxy, ester, thiol, primary or secondary amino or amido groups, or
  a phenyl or an aryl residue, R⁵ being optionally substituted with a biologically active substance, wherein said biologically active substance is selected among sugars, amino acids, fatty acids, vitamins, hormones, peptides, catecholamines, said catecholamines being optionally conjugated, via peptidic bond, to another of the above mentioned biologically active substances;
n is an integer ranging from 1 to 5;
L² is a bidentate ligand, which comprises a combination of two donor atoms, selected from the group consisting of oxygen, sulphur and nitrogen, said atoms being preferably negatively charged and being separated by a spacer of 2 to 4 members, said spacer being an aliphatic chain or part of an aromatic ring, L² being optionally conjugated to a biologically active substance as above defined;
Z⁻ is a mononegative counter-ion selected from the group consisting of Cl⁻, Br⁻, OH⁻, ClO₄⁻, EtO⁻, tetrafluoroborate.

2. A radioactive transition metal-imido hetero-diphosphine complex according to claim 1, wherein the radioactive transition metal is $^{99m}$Tc.

3. A complex according to claim 1, wherein dopamine is conjugated to vitamin H.

4. A radioactive transition metal-imido hetero-diphosphine complex according to claim 1, wherein L¹ is selected from the group consisting of:
  $(C_6H_5)_2PCH_2CH_2N(H)CH_2CH_2P(C_6H_5)_2$;
  $(C_6H_5)_2PCH_2CH_2N(CH_3)CH_2CH_2P(C_6H_5)_2$;
  $(C_6H_5)_2PCH_2CH_2N(CH_2CH_2OCH_3)CH_2CH_2P(C_6H_5)_2$;
  $(CH_3)_2PCH_2CH_2N(CH_3)CH_2CH_2P(CH_3)_2$;
  $(C_6H_5)_2PCH_2CH_2SCH_2CH_2P(C_6H_5)_2$;
  $(C_6H_5)_2PCH_2CH_2OCH_2CH_2P(C_6H_5)_2$.

5. A radioactive transition metal-imido hetero-diphosphine complex according to claim 1, wherein L² comprises a combination of two electron-donor atoms selected from the group consisting of [O⁻,O⁻], [N⁻,O⁻], [S⁻,O⁻], [N⁻,N⁻], [N⁻,S⁻] and [S⁻,S⁻], said atoms being separated by a 2 to 4 membered spacer, wherein said spacer is an aliphatic chain or part of an aromatic ring.

6. A complex according to claim 5, wherein L² is selected from the group consisting of catecholate$^{(2-)}$; carbonate$^{(2-)}$; 1,2-phenylenediaminate$^{(2-)}$; 1,2-benzenedithiolate$^{(2-)}$; ethyleneglycolate$^{(2-)}$; ethylenediaminate$^{(2-)}$; ethylenedithiolate$^{(2-)}$; 1,2-aminophenolate$^{(2-)}$; 1,2-aminothiophenolate$^{(2-)}$; thiosalicilate$^{(2-)}$; 1,2-aminoethanolate$^{(2-)}$.

7. A complex according to claim 5, wherein L² is conjugated to a catecholamine selected from the group consisting of dopamine, L-DOPA, 3-hydroxytyramine, optionally conjugated to another biologically active substance selected from the group consisting of sugars, amino acids, fatty acids, vitamins, hormones, peptides, and catecholamines.

8. A complex according to claim 7, wherein dopamine is conjugated to vitamin H.

9. A radioactive transition metal-imido hetero-diphosphine complex according to claim 1, wherein Z⁻ is Cl⁻, ClO₄⁻, EtO⁻, tetrafluoroborate.

10. A radioactive transition metal-imido hetero-diphosphine complex of claim 1 for use in radiodiagnostic imaging.

11. A radioactive transition metal-imido hetero-diphosphine complex of claim 1 for use in radiotherapy.

12. A pharmaceutical composition comprising a radioactive transition metal-imido hetero-diphosphine complex of claim 1 in admixture with pharmaceutically acceptable carriers and/or excipients.

* * * * *